United States Patent [19]

Shepherd et al.

[11] 4,145,254

[45] Mar. 20, 1979

[54] RED PIGMENT PRODUCTION

[75] Inventors: David Shepherd, Morges; Mariette S. C. Carels, Orbe, both of Switzerland

[73] Assignee: Societe d'Assistance Technique pour Produits Nestle S.A., La Toure de Peilz, Switzerland

[21] Appl. No.: 800,354

[22] Filed: May 25, 1977

[30] Foreign Application Priority Data

Jun. 2, 1976 [CH] Switzerland ................. 6919/76

[51] Int. Cl.$^2$ ..................... C12D 13/02; A23L 1/27
[52] U.S. Cl. ................................. 195/81; 426/250
[58] Field of Search ............................ 195/81

[56] References Cited

U.S. PATENT DOCUMENTS

| | | | |
|---|---|---|---|
| 3,765,906 | 10/1973 | Yamaguchi et al. | 195/81 X |
| 3,993,789 | 11/1976 | Moll et al. | 426/250 |

OTHER PUBLICATIONS

Ishibashi et al., Chemical Abstract, vol. 85, 175615m (1976), of Japan Kokai, 76 67,793, Jun. 11, 1976.

*Primary Examiner*—Lionel M. Shapiro
*Attorney, Agent, or Firm*—Watson, Leavenworth, Kelton & Taggart

[57] ABSTRACT

A process for producing a Monascus pigment by growing a microorganism of the genus Monascus in an aqueous nutrient medium under aerobic conditions. The microorganism is grown at a pH-value in the range from 4 to 7 in a first medium which promotes its growth; a first biomass is obtained; the first biomass thus obtained is transferred to a second medium which stimulates the production of pigment; the pH is adjusted to a value in the range from 2 to 4; the growth process is continued for a period of 2 to 7 days at a temperature in the range from 20° to 35° C. and pigment is extracted with a solvent from the second biomass obtained.

5 Claims, No Drawings

RED PIGMENT PRODUCTION

This invention relates to a process for the production of a Monascus pigment by growing a microorganism of this genus in an aqueous nutrient medium under aerobic conditions.

It has long been known that microorganisms of the genus Monascus produce red pigments which can be used for colouring foods. In certain oriental countries, microorganisms of this type are grown on grains of rice and, once the grains of rice have been penetrated by the red mycelium, the whole is finely ground. The powder obtained is used for colouring inter alia wines and soya cheeses.

In view of the strong colouring power of this natural colorant, numerous studies have been made either of the composition and structure of the constituent molecules of these pigments, or of the growth of the microorganisms themselves. Both the exact structure of these pigments and some of their chemical properties are now known. For example, it is known that the red pigment emanates from the reaction of an orange pigment, such as monascorubrin or rubropunctatin, with an ammonium ion or an amino group of the type present in an amino acid, an amino sugar, polymers of amino sugars, polyamino acids or amino alcohols.

These studies and findings have permitted the development of processes for producing Monascus pigments on an industrial scale. Thus, in one recently developed process, a microorganism of the genus *Monascus anka* or *Monascus purpureus* is grown under aerobic conditions in an aqueous nutrient medium containing, as nitrogen source, rice powder, an extract of yeast, a peptone or ammonium sulphate for example, the mycelium is harvested, the pigment is extracted from the mycelium with an organic solvent, such as alcohol, and the pigment is reacted with a soluble protein or with soluble peptides to obtain a water-soluble pigment. Although this process represents a significant advance in the definition of the product obtained over the colour powders obtained by previous processes, it is still attended by considerable disadvantages. Its most obvious disadvantage is that part of the orange pigment which it is desired to collect for subsequent reaction with a protein actually reacts with intracellular proteins within the mycelium itself, or amino acids in the culture medium. This makes the pigment difficult to extract and reduces the yield of orange pigment.

Now, if it is desired commercially to obtain a pigment having a perfectly determined structure which may be subjected to rigorous tolerance tests and which shows perfectly reproducible properties, it is the high-yield production of a high-purity orange pigment which should be researched in the first instance.

The present invention is the outcome of such research.

The present invention provides a process for producing a Monascus pigment by growing a microorganism of the genus Monascus in an aqueous nutrient medium under aerobic conditions, wherein the microorganism is grown at a pH-value in the range from 4 to 7 in a first medium which promotes its growth; a first biomass is obtained; the first biomass thus obtained is transferred to a second medium which stimulates the production of pigment; the pH is adjusted to a value in the range from 2 to 4; the growth process is continued for a period of 2 to 7 days at a temperature in the range from 20 to 35° C. and pigment is extracted with a solvent from the second biomass obtained.

Accordingly, the process according to the invention comprises two phases, the first being a growth phase of the microorganism under conditions which are capable of completely inhibiting the production of secondary metabolites, such as the pigment in question, and the second being a production phase of the desired pigment under conditions which are capable of promoting this production. Accordingly, the biomass referred to in the context of the invention as the first biomass may be weakly coloured or even colourless, whilst the biomass referred to as the second biomass represents as it were a subsequent stage of the first biomass and which is coloured.

By virtue of the process according to the invention, it is possible to obtain an orange pigment of high purity which is capable of being subsequently used for the production of a red pigment with a perfectly determined structure by reaction with a suitable pure substance such as, for example, a given amino acid, aminopolysaccharide or amino alcohol.

It has been found that if the pH of the culture medium is kept at a value in the range from 2 to 4 during the phase of production of the pigment by the microorganism, the abovementioned reaction between the orange pigment and ammonium ion or amino group is inhibited. It has been found that hardly any pigment such as rubropunctatamine or monascorubramine is formed in this way, instead there is almost exclusively obtained a pigment such as rubropunctatin or monascorubrin, namely an orange pigment which has a maximum absorption at a wavelength of 470 nm. In addition, the quantity of orange pigment produced may reach a remarkable level, amounting for example to as much as 3 mg per ml of culture medium.

It has also been found that, by keeping the pH of the culture medium at a value in the range from 2 to 4, the production of conidia is inhibited. In other words, the production of a pigment such as rubropunctatin or monascorubrin is accompanied in the present case by an inhibition of the production of conidia. More precisely, it has been found that, by adjusting the pH to a value in the range from 2 to 4, formation of the lipids necessary for the production of conidia is limited. In other words, since the respective productions of conidia and pigment compete for the use of fatty acids, the inhibition of the formation of lipids is reflected in a stimulating effect on the production of pigments. Accordingly, the formulation of the process according to the invention could fall within the scope of a more general definition according to which steps are taken to limit the production of conidia thereby increasing the amount of the pigments in question.

Any strain of a microorganism of the genus Monascus which produces pigment of the monascorubrin or rubropunctatin type may be used for carrying out the process according to the invention. An inoculum of the strain selected may be prepared from a reconstituted freeze-dried culture or from a culture on a solid medium by any method known to the expert. The inoculum prepared contains a quantity of mycelium which is adapted to the dimensions of the installation in which it is intended to grow the mycelium. For example, in the case of shaked flasks with a capacity of a few deciliters or even liters, the mycelium may be removed from the solid medium and homogenised with a few tens of ml of medium to be inoculated. In the context of the invention, a solid medium is a culture medium comprising a usual carbon source, such as glucose, an organic nitrogen source and growth factors in the form of an extract of yeast for example and agar as solidifier.

The inoculum thus prepared may be introduced into a first aqueous culture medium containing from 1 to 10% by weight and preferably 4% by weight of glucose and from 0.1 to 2% by weight of an amino acid source, preferably 1% of yeast extract. The inoculated medium may be incubated at a temperature of from 20 to 35° C. and preferably at a temperature of 25° C. under suitable conditions of aeration and agitation for a period of time sufficient to obtain good growth of the mycelium, but without any formation of pigment, namely for a period of time of the order of 24 hours. It is also possible to carry out this growth phase in the first medium in several steps, more especially two, each lasting from 24 to 48 hours in two successive bottles. The mycelium may then be transferred to a second aqueous medium containing from 0.5 to 10% by weight and preferably 3% by weight of glucose and from 0.05 to 5% by weight, preferably 0.15% by weight, of an ammonium salt and/or a nitrate and all the oligoelements necessary for or capable of ensuring maximum growth and maximum production of pigment. The pH of the second medium may be adjusted to a value in the range from 2 to 4 by adding the necessary quantity of acid, the type of acid used for this purpose being of no real importance. In cases where the nitrogen source used is an ammonium salt, the pH may be allowed to fall to a value of from 2 to 4 in consequence of the consumption of the ammonium ion by the microorganism. The growth process may be continued in the second medium for a period of time sufficient to reach a maximum production level of pigments. This period of time is of the order of 2 to 7 days. The temperature is kept at a value in the range from 20° C. to 35° C and preferably at a value of 25° C.

The mycelium, the second biomass, may then be separated from the second medium by any adequate method such as, for example, filtration or centrifuging, and the orange pigment may be extracted therefrom with a suitable solvent such as, for example, ethanol, methanol, chloroform or methylene dichloride. However, it has been found that a maximum extraction yield may be obtained by homogenising the mycelium with the culture broth, in other words by homogenising the suspension of second biomass in the second medium and by extracting the pigment from the homogenised suspension with a suitable solvent of the type mentioned above. If this procedure is adopted, it is advisable to adjust the pH to a value of from 2 to 3 before extraction in order to obtain an orange pigment with maximum purity, in other words to avoid partial conversion of the orange pigment into red pigment.

The invention is illustrated by the following Examples in which the percentages quoted represent % by weight.

EXAMPLE 1

The strain *Monascus rubiginosus* ATCC 16367 is grown on a solid medium containing 4% of glucose, 1% of yeast extract, 0.3% of $KH_2PO_4$ and 1.5% of agar. After incubation for 1 week at 30° C., the mycelium is collected. It is homogenised with 30 ml of an aqueous culture medium containing 4% of glucose, 1% of yeast extract and 0.1% of $KH_2PO_4$. The inoculum thus prepared is introduced into a 500 ml-capacity flask containing 150 ml of the same aqueous culture medium as that used for homogenisation. Incubation is then carried out over a period of 24 hours at 25° C. on a rotary agitator rotating at 150 rpm. 10 ml of the suspension obtained are introduced into a flask containing 150 ml of an aqueous medium containing 3% of glucose, 0.15% of $NH_4Cl$, 0.1% of $KH_2PO_4$, 0.05% of $MgSO_4.7H_2O$, 0.05% of NaCl and 0.01% of $FeSO_4.7H_2O$ prepared with distilled water and sterilised for 20 minutes at 121° C. Incubation is then carried out at 25° C. on a rotary agitator rotating at 150 rpm. In 24 hours, the nitrogen content of the medium falls from 41.5 mg/100 ml to 30 mg/100 ml and the pH falls to 2.9, after which the production of pigment commences. The production of pigment reaches its maximum, 2.5 mg/ml, after 120 hours. The pigment is extracted with 50% ethanol. An orange solution containing a single pigment is obtained.

EXAMPLES 2 to 7

Different species and different strains of Monascus (M.) are grown and the pigment is extracted therefrom in the same way as described in Example 1, except for the fact that the second aqueous culture medium is slightly different and contains 4% of glucose, 0.05% of $NH_4Cl$, 0.1% of $KH_2PO_4$, 0.05% of $MgSO_4.7H_2O$, 0.05% of NaCl and 0.01% of $FeSO_4.7H_2O$. The results set out in the following Table are obtained. The column headed "pigment" shows in mg per ml of culture medium the quantity of orange pigment produced after incubation for 7 days in the second medium. The column headed "pH after 24 h" shows the value to which the pH has fallen in the second culture medium after incubation for 24 hours in that medium.

| Example No. | Monascus species Name | ATCC No. | Pigment after 7 days mg/ml | pH after 24 h |
|---|---|---|---|---|
| 2 | M. purpureus | 6405 | 0.62 | 2.95 |
| 3 | M. major | 16362 | 1.47 | 2.45 |
| 4 | M. purpureus | 16365 | 1.7 | 2.6 |
| 5 | M. rubiginosus | 16367 | 2.35 | 2.55 |
| 6 | M. purpureus | 16427 | 1.26 | 2.7 |
| 7 | M. species | 16435 | 1.41 | 2.95 |

EXAMPLES 8 to 18

Several inocula of the strains *Monascus major* ATCC 16362 and *Monascus rubiginosus* ATCC 16367 are prepared. To prepare each inoculum, the strain is grown on a solid medium containing 4% of glucose, 0.3% of $KH_2PO_4$, 1% of yeast extract and 1.5% of agar, the rest being distilled water held in the gel. After incubation for 6 days at 25° C., the mycelium is collected from the solid medium. It is mixed with 30 ml of a liquid culture medium I having the same composition as the above-mentioned solid culture medium except for the fact that it does not contain agar, and the mixture is homogenised for 45 seconds in a 50 ml chamber of a homogeniser of the SORVAL OMNIMIXER type.

Mycelia in a state of growth are prepared from these inocula. To this end, each inoculum is introduced into a 500 ml capacity flask containing 150 ml of medium I. Incubation is carried out over a period of 48 hours at 25° C. on a rotary agitator rotating at 150 rpm. 10 ml of the suspension obtained are removed, introduced into another 500 ml capacity agitation bottle containing 150 ml of medium I and incubated for another 24 hours at 25° C.

Three aqueous culture media, II, III and IV are prepared, in which the nitrogen source is an ammonium salt or a nitrate. Medium II contains 0.3% of $NaNO_3$, medium III contains 0.05% of $NH_4Cl$ and medium IV contains 0.2% of $NH_4NO_3$. Apart from this, the three media are identical and each contain 4% of glucose, 0.1% of $KH_2PO_4$, 0.05% of $MgSO_4.7H_2O$, 0.05% of NaCl and 0.01% of $FeSO_4.7H_2O$. The three media are prepared with distilled water and are sterilised for 15 minutes at 121° C. After sterilisation, the media II, III and IV have respective pH-values of 5.0, 5.2 and 5.3 unless the pH is intentionally reduced before sterilisation.

The two above-mentioned mycelia in a state of growth are then grown in these various media capable of promoting the production of pigment. This second phase of the growth process is carried out in the same way for the various tests except for the fact that the pH-conditions are varied. 10 ml of the mycelium suspension obtained after the second 24 hour incubation in medium I are used for each test. These 10 ml are introduced into a 500 ml capacity flask containing 150 ml of medium II, III or IV. Incubation is carried out at a temperature of 25° C. over the period of time required to obtain a maximum production of pigment. The pH-value is optionally lowered with HCl to pH 2.5 before and, in some cases, even during this incubation. A coloured mycelium suspension is obtained. It is homogenised for 30 seconds in a homogeniser of the SORVAL OMNIMIXER type. The pH-value is adjusted to 2.5. The pigment is extracted from the homogenised suspension with ethanol in a quantity of 10 parts by volume of 50% ethanol to 1 part by volume of suspension. The mycelium is eliminated by filtration. The concentration of orange pigment is measured by spectrophotometric absorption. The results obtained and also the particulars of the various tests are set out in the following Table.

In the column headed "pH-lowered" under the subheading "when", the abbreviations "bef. ster.", "+ after 24 h" and "+ after 48 h" mean that the pH-value was respectively lowered before sterilisation of the medium and after culture for 24 hours or 48 hours in the medium in question. Tests 8 to 14 were carried out with the strain ATCC 16367 and tests 15 to 18 with the strain ATCC 16362.

| Ex. No. | Strain | Medium | pH-lowered to 2.5 | when | Pigment mg/ml | Culture time (days) |
|---|---|---|---|---|---|---|
| 8 | ATCC 16367 | II | no | — | 1.56 | 3 |
| 9 | | II | yes | bef.ster. | 1.76 | 3 |
| 10 | | II | yes | bef.ster + after 24 h | 2.52 | 3 |
| 11 | | II | yes | bef.ster + after 48 h | 2.84 | 4 |
| 12 | | III | yes | bef.ster | 2.30 | 4 |
| 13 | | IV | no | — | 1.68 | 3 |
| 14 | | IV | yes | bef.ster. | 2.18 | 4 |
| 15 | ATCC 16362 | II | no | — | 0.88 | 4 |
| 16 | | II | yes | bef.ster. | 1.13 | 3 |
| 17 | | II | yes | bef.ster. + after 24 h | 1.68 | 4 |
| 18 | | II | yes | bef.ster. + after 48 h | 1.60 | 4 |

We claim:

1. A process for producing an orange Monascus pigment by growing a microorganism of the genus Monascus in an aqueous nutrient medium under aerobic conditions, wherein the microorganism is grown at a pH-value in the range from 4 to 7 in a first medium which promotes its growth; a first biomass is obtained; the first biomass thus obtained is transferred to a second medium which stimulates the production of pigment; the pH is controlled to a value in the range from 2 to 4 which inhibits the reaction of the produced orange pigment with the medium to prevent production of reg pigment; the growth process is continued for a period of 2 to 7 days at a temperature in the range from 20° to 35° C. and orange pigment is extracted with a solvent from the second biomass obtained.

2. A process as claimed in claim 1, wherein the first medium contains an organic nitrogen source and growth factors.

3. A process as claimed in claim 1, wherein the second medium contains nitrate and/or an ammonium salt as nitrogen source.

4. A process as claimed in claim 1, wherein a suspension of the second biomass is homogenised in the second medium, the pH is adjusted to a value of from 2 to 3 and pigment is extracted from the homogenised suspension.

5. An orange Monascus pigment when prepared by a process as claimed in claim 1.

* * * * *

UNITED STATES PATENT AND TRADEMARK OFFICE
CERTIFICATE OF CORRECTION

PATENT NO. : 4,145,254
DATED : March 20, 1979
INVENTOR(S) : David Shepherd and Mariette Suzanne Catherine Carels It is certified that error appears in the above-identified patent and that said Letters Patent are hereby corrected as shown below:

Claim 5 should be deleted.

Signed and Sealed this

Twenty-second Day of January 1980

[SEAL]

*Attest:*

*Attesting Officer*

SIDNEY A. DIAMOND
*Commissioner of Patents and Trademarks*